(12) United States Patent
Zhu et al.

(10) Patent No.: US 8,895,237 B2
(45) Date of Patent: Nov. 25, 2014

(54) ENHANCING OF HEPATITIS B VIRUS VACCINE AND ITS GENE

(75) Inventors: Naishuo Zhu, Shanghai (CN); Huaqing Li, Shanghai (CN); Min Yang, Shanghai (CN)

(73) Assignee: Fudan University, Shanghai (CN)

( * ) Notice: Subject to any disclaimer, the term of this patent is extended or adjusted under 35 U.S.C. 154(b) by 1302 days.

(21) Appl. No.: 12/282,754

(22) PCT Filed: Mar. 16, 2007

(86) PCT No.: PCT/CN2007/000844
§ 371 (c)(1),
(2), (4) Date: Jan. 14, 2009

(87) PCT Pub. No.: WO2007/104263
PCT Pub. Date: Sep. 20, 2007

(65) Prior Publication Data
US 2010/0055135 A1    Mar. 4, 2010

(30) Foreign Application Priority Data

Mar. 16, 2006   (CN) .......................... 2006 1 0024756

(51) Int. Cl.
| | | |
|---|---|---|
| *C12Q 1/00* | (2006.01) | |
| *A61K 39/29* | (2006.01) | |
| *C07K 14/47* | (2006.01) | |
| *A61K 38/00* | (2006.01) | |
| *A61K 39/00* | (2006.01) | |

(52) U.S. Cl.
CPC .............. *C07K 14/4705* (2013.01); *A61K 38/00* (2013.01); *C12N 2730/10134* (2013.01); *A61K 39/292* (2013.01); *A61K 2039/55516* (2013.01)
USPC .......................................... 435/4; 424/227.1

(58) Field of Classification Search
None
See application file for complete search history.

(56) References Cited

FOREIGN PATENT DOCUMENTS

WO    WO/2005/044304    *    5/2005

OTHER PUBLICATIONS

Budkowska, A., et al., "Activation of the envelop proteins by a metalloproteinase enables attachment and entry of the hepatitis B virus into T-lymphocyte," Virology, vol. 27, pp. 10-22 (1997).
Chen, Y.Y, et al., "Screening, expression and characterization of a novel protein binding to hepatitis B surface antigen," Chinese Journal of Biochemistry and Molecular Biology, vol. 21, pp. 53-60 (Feb. 2005).
GenBank Accession No. AY570731, Apr. 14, 2004, 1 page. Cited in the International Search Report for corresponding PCT/CN2007/000884.
PCT Search Report mailed on Jun. 28, 2007 from PCT/CN2007/000844, and its English translation.
PCT Written Opinion of the International Search Authority mailed on Jun. 28, 2007 from PCT/CN2007/000844, and its English translation.
Chapter I PCT International Preliminary Report on Patentability dated Sep. 16, 2008 from PCT/CN2007/000844, and its English translation.

* cited by examiner

*Primary Examiner* — Padma V Baskar
(74) *Attorney, Agent, or Firm* — Ladas & Parry, LLP

(57) ABSTRACT

This invention relates to a HB vaccine enhancing protein, its gene, gene engineering method for expressing this protein, and the application of this method. The cDNA of this protein, which is screened out from human liver cDNA library, is sequenced and then cloned into prokaryotic or eukaryotic (animal or plant) cell for expression of protein coded by the cDNA (for example, cloning into prokaryotic expression carrier and expression in *E. coli*) and purification of the protein. The protein obtained, when used with HB vaccine, can significantly increase the effect of the vaccine, the immune power of HBV carrier, and the titer of antibody. The protein can be used as an adjutant to HB vaccine.

2 Claims, 1 Drawing Sheet

ENHANCING OF HEPATITIS B VIRUS VACCINE AND ITS GENE

FIELD OF THE INVENTION

This invention relates to a protein that binds to hepatitis B virus (HBV) with high specificity and promotes immune response to hepatitis B virus vaccine, the gene that encodes the protein, and application of the protein in the prevention, diagnosis and treatment of relevant diseases.

DESCRIPTION OF RELATED ARTS

Hepatitis B is an infectious disease of high incidence and grave consequences, and a serious threat to public health. Vaccination is the most effective measure to prevent HBV infection and reduce the carrier rate of HBV. However, immune response to hepatitis B vaccine varies significantly across different individuals. In many people receiving the standard 6-month 3-dose vaccination regimen, not enough antibody was produced to offer protection. Therefore, finding molecules that could effectively promote the immunogenicity of hepatitis B vaccine and to enhance the immune response is an important way to solve the problem.

Genetic engineering using either prokaryotic expression system (e.g., *E. coli*) or eukaryotic expression system (e.g., mammalian cells) is the most effective way to obtain a large quantity of a specific protein. The gene is identified by screening a cDNA expression library. The protein encoded by the gene is obtained by gene cloning, expression and purification. Obtained protein is used in combination with HBV vaccine to immunize animal. Titer of hepatitis B surface antibody in immunized animal is detected by ELISA. This is a convenient way to determine whether a protein can promote the immune response to HBV vaccine, and therefore its potential for use in human subjects.

SUMMARY OF THE INVENTION

The aim of the present invention is to provide a protein enhancing hepatitis B vaccine, its gene and methods to express and apply this protein.

The gene sequence and amino acid sequence of the protein enhancing HB vaccine are SEQ.ID.NO.1 and SEQ.ID.NO.2 respectively.

The inventor screened out the gene above-mentioned from human liver cDNA expression library and expressed it using gene engineering method. The approach is as follows:

Obtaining the protein and cDNA gene that codes the protein: A positive cDNA clone is obtained by screening a human liver cDNA expression library using immunobloting against the surface antigen of hepatitis B. Analysis of the cDNA sequence revealed an independent open reading frame (ORF) of 1035 bp. Further experiments proved that the protein encoded by the cDNA can specifically bind to the hepatitis B surface antigen. The protein is named as hepatitis B virus surface antigen binding protein (HBsAg binding protein, SBP).

The ORF of the cDNA was attached with 6×his purification tag and enterokinase cleavage site DDDDK at the N-terminus, then cloned into prokaryotic expression system pBV220. Protein expression was induced in *E. coli* at optimal temperature. *E. coli* was collected and lysed, and inclusion bodies were extracted, roughly purified, and then purified using Ni-NTA agarose and affinity chromatography. After refolding using dialysis method, the target protein was obtained.

Effects of SBP on the immune response to hepatitis B vaccine: experimental animals were divided into a test and a control group. Mice, for example, were immunized using a conventional method with hepatitis B vaccine. Two boost vaccine injections were given subcutaneously at the 10th and 17th day after the initial dose. The test group received subcutaneous injection of SBP every three days. The controls did not receive SBP. At the 20th day after the initial does for immunization, blood was obtained from the tail vein. Titer of the antibody against the hepatitis B surface antigen in the serum was detected by ELISA. A SPSS software was used to analyze the group differences. The results indicated that the proteins can significantly increase the titer of antibody in mice. In other words, the proteins can enhance the immune response to hepatitis B vaccine (FIG. 2).

Therefore, SBP can be used to promote the immunogenicity of hepatitis B virus vaccine, and to increase the titer of the antibody against the hepatitis B surface antigen. Consequently, the SBP could be used as adjuvants of hepatitis B virus vaccine. Combined use of SBP with hepatitis B virus vaccine could enhance the immune response to hepatitis B virus vaccine, and reduce dosage and frequency of the vaccination. The fact that SBP could bind to the hepatitis B surface antigen with high specificity and increase the titer of anti-surface antibody suggests that SBP could be used to enhance the efficacy of patient/carrier treatment, and to develop therapeutic vaccines. In addition, the SBP can also be used for research purposes. For example. these SBP could be used to produce monoclonal antibodies (mAb) for detecting endogenous SBP as an index for immune functions.

THE DETAILED DESCRIPTION OF THE PREFERRED EMBODIMENT

Figure 1:
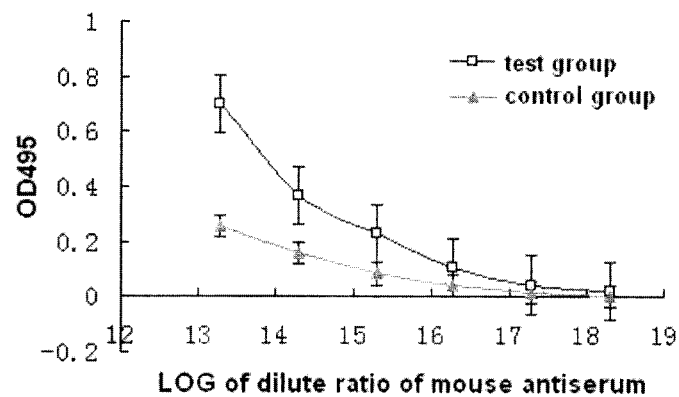
FIG. 1. Effect of SBP on the titer of anti-HBsAg antibody in Balb/c mouse (I).
Figure 2:
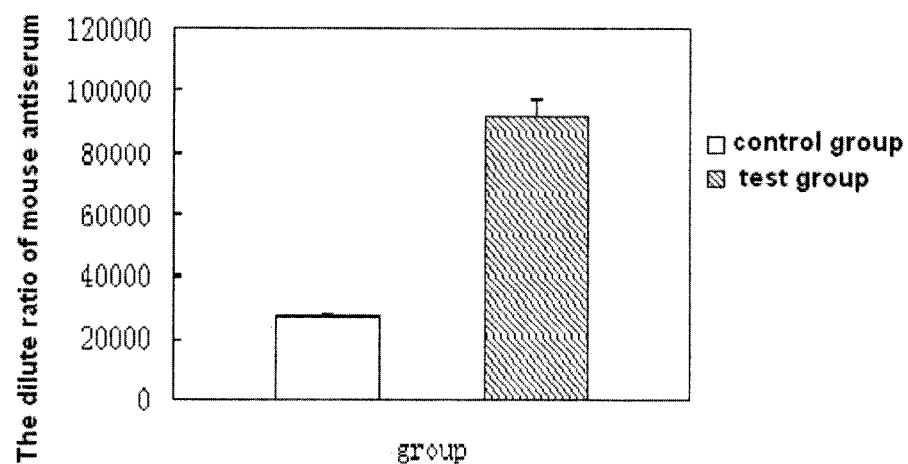
FIG. 2. Effect of SBP on the titer of anti-HBsAg antibody in Balb/c mouse ( ). Balb/c mice of the same age receiving no treatment were used as controls. $OD_{495}$ value 10 times higher than the control value (0.13) was considered positive. Anti-HBsAg antibody titer was calculated according to the OD values and serum dilution multiples using an one dimension regression. The titer of anti-HBsAg antibody in the test group (n=5) was $9.24 \times 10^4$. The titer in the control mice (n=5) was $2.68 \times 10^4$. The difference was significant as revealed by an independent sample t-test (P<0.04). Therefore, the SBP was able of increasing the HBsAg antibody titer in mice.

The preparation of the gene sequences:

A cDNA clone encoding hepatitis B surface antigen binding protein was obtained by screening a human liver cDNA phage expression library with a complete hepatitis B surface antigen (including the pre-S1, pre-S2 and S zones) purified from human plasma by immunobloting. Gene sequencing results revealed an independent open reading frame (ORF) of 1035 bp (SEQ.ID.NO.1) in the cDNA that encodes 344 amino acid residues, with a theoretical molecular weight of about 38 ku. The isoelectric point (PI) was 8.0. Deduced sequence indicated typical transmembrane regions and classification into the immunoglobulin superfamily. The sequence of the protein encoded by the ORF is SEQ.ID.NO.2.

Expression and Purification:

Protein was expressed and purified after the gene mentioned above was cloned into prokaryotic or eukaryotic expression vectors. The entire gene was cloned into the pBV220 prokaryotic expression vector. *E. Coli* were transfected with the recombinant vector. Positive monoclones were cultured in liquid culture medium. Protein expression was induced at 37 firstly then 42 for 5 h. Proteins were purified with Ni-NTA agarose affinity columns. Purified protein was re-natured by dialysis. Interaction of the proteins with target was verified with ELISA and Western blotting.

Evaluation of the Effect of the Prepared Protein on HB Vaccine:

Balb/c mice (age: 7 weeks; half male and half female) are divided into test group and control group. HB vaccine is injected into mice subcutaneously using common method. The injection protocol is shown in the table below.

| Vaccine injection (subcutaneous injection) | Interval | Test group | Control group |
|---|---|---|---|
| First injection | | HBsAg 80 μg, SBP 2 μg | HBsAg 80 μg |
| | 3 days | SBP 6 μg | |
| | 6 days | SBP 9.5 μg | |
| Second injection | 9 days | HBsAg 120 μg, SBP 7.5 μg | HBsAg 120 μg |
| | 12 days | SBP 65 μg | |
| | 15 days | SBP 75 μg | |
| Third injection | 16 days | HBsAg 120 μg | HBsAg 120 μg |
| | 17 days | SBP 75 μg | |

Blood was obtained from tail vein on the 20th day after the first immunization, The antibody level against the hepatitis B surface antigen in the serum was determined by ELISA. A SPSS software was used to analyze the group differences.

The results (refer to FIG. 1 and FIG. 2) showed that the anti-surface antibody titer in the test group was $9.24\times10^4$ on the 20th day after the initial immunization, and significantly higher than that in the controls ($2.68\times10^4$). This result indicated that the protein can significantly up-regulate the level of anti-surface antibody in mice, and augment the immune response the hepatitis B vaccine.

Application:

Immune response to hepatitis B vaccine varies significantly across different individuals. In many people receiving the standard 6-month 3-dose vaccination regimen, not enough antibody was produced to offer protection. The proteins described in this invention can significantly augment the immune response to hepatitis B vaccine. Accordingly, these proteins can be used to develop hepatitis B vaccine adjuvant or directly in combination with the hepatitis B vaccines that are currently available. Simultaneous use of a certain mount of SBP with hepatitis B vaccine can increase the immunogenicity of the vaccine, and increase the titer of neutralizing antibodies. SBP has specific affinity to hepatitis B surface antigen, and can increase the production of the antibody against hepatitis B surface antigen. As a result, SBP can also be used for the treatment of patients and carriers of hepatitis B virus. SBP could also be valuable in research to develop therapeutic hepatitis B vaccines.

What is claimed is:

1. A method of producing an enhanced Hepatitis B virus (HBV) vaccine, the method comprising:

combining a first polypeptide having an amino acid sequence of a Hepatitis B surface antigen (HBsAg) with a second polypeptide having an amino acid sequence of a recombinant Hepatitis B surface antigen binding protein (SBP) to produce an enhanced HBV vaccine, wherein the second polypeptide consisting of an amino acid sequence of SEQ.ID.NO.2 as an adjuvant, and the enhanced HBV vaccine has greater immunogenicity than the HBsAg itself.

2. The method of producing an enhanced HBV vaccine of claim 1, wherein the second polypeptide is encoded by the polynucleotide sequence of SEQ.ID.NO.1.

* * * * *

SEQUENCE LISTING

```
<160> NUMBER OF SEQ ID NOS: 2

<210> SEQ ID NO 1
<211> LENGTH: 1035
<212> TYPE: DNA
<213> ORGANISM: Homo sapiens

<400> SEQUENCE: 1
atggacgtct ggggccaagg gaccacggtc accgtctcct cagcctccac caagggccca     60
tcggtcttcc ccctggcacc ctcctccaag agcacctctg ggggcacagc ggccctgggc    120
tgcctggtca aggactactt ccccgaaccg gtgacggtgt cgtggaactc aggcgccctg    180
accagcggcg tgcacacctt cccggctgtc ctacagtcct caggactcta ctccctcagc    240
agcgtggtga ccgtgccctc cagcagcttg ggcacccaga cctacatctg caacgtgaat    300
cacaagccca gcaacaccaa ggtggacaag agagttgagc ccaaatcttg tgacaaaact    360
cacacatgcc caccgtgccc agcacctgaa ctcctggggg gaccgtcagt cttcctcttc    420
cccccaaaac ccaaggacac cctcatgatc tcccggaccc ctgaggtcac atgcgtggtg    480
gtggacgtga gccacgaaga ccctgaggtc aagttcaact ggtacgtgga cggcgtggag    540
gtgcataatg ccaagacaaa gccgcgggag gagcagtaca acagcacgta ccgtgtggtc    600
agcgtcctca ccgtcctgca ccaggactgg ctgaatggca aggagtacaa gtgcaaggtc    660
tccaacaaag ccctcccagc ccccatcgag aaaaccatct ccaaagccaa agggcagccc    720
cgagaaccac aggtgtacac cctgccccca tcccgggagg agatgaccaa gaaccaggtc    780
agcctgacct gcctggtcaa aggcttctat cccagcgaca tcgccgtgga gtgggagagc    840
aatgggcagc cggagaacaa ctacaagacc acgcctcccg tgctggactc cgacggctcc    900
ttcttcctct atagcaagct caccgtggac aagagcaggt ggcagcaggg gaacgtcttc    960
tcatgctccg tgatgcatga ggctctgcac aaccactaca cgcagaagag cctctccctg   1020
```

```
tccccgggta aatga                                                    1035
```

<210> SEQ ID NO 2
<211> LENGTH: 344
<212> TYPE: PRT
<213> ORGANISM: Homo sapiens

<400> SEQUENCE: 2

```
Met Asp Val Trp Gly Gln Gly Thr Thr Val Thr Val Ser Ser Ala Ser
1               5                   10                  15

Thr Lys Gly Pro Ser Val Phe Pro Leu Ala Pro Ser Ser Lys Ser Thr
            20                  25                  30

Ser Gly Gly Thr Ala Ala Leu Gly Cys Leu Val Lys Asp Tyr Phe Pro
        35                  40                  45

Glu Pro Val Thr Val Ser Trp Asn Ser Gly Ala Leu Thr Ser Gly Val
    50                  55                  60

His Thr Phe Pro Ala Val Leu Gln Ser Ser Gly Leu Tyr Ser Leu Ser
65                  70                  75                  80

Ser Val Val Thr Val Pro Ser Ser Ser Leu Gly Thr Gln Thr Tyr Ile
                85                  90                  95

Cys Asn Val Asn His Lys Pro Ser Asn Thr Lys Val Asp Lys Arg Val
            100                 105                 110

Glu Pro Lys Ser Cys Asp Lys Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Ala Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340
```